United States Patent
Sakamoto (10) Patent No.: US 7,744,529 B2
(45) Date of Patent: Jun. 29, 2010

(54) LARYNGOSCOPE BLADE

(75) Inventor: Carl Kaoru Sakamoto, 83 E. Pleasant Lake Rd., North Oaks, MN (US) 55127

(73) Assignee: Carl Kaoru Sakamoto, North Oaks, MN (US)

( * ) Notice: Subject to any disclaimer, the term of this patent is extended or adjusted under 35 U.S.C. 154(b) by 1069 days.

(21) Appl. No.: 10/777,293

(22) Filed: Feb. 12, 2004

(65) Prior Publication Data

US 2005/0182300 A1     Aug. 18, 2005

(51) Int. Cl.
    *A61B 1/267* (2006.01)
(52) U.S. Cl. ............... 600/190; 600/185; 600/191; 600/193; 600/194; 600/195; 600/196; 600/197
(58) Field of Classification Search .......... 600/185, 600/190, 195, 196, 201, 210
See application file for complete search history.

(56) References Cited

U.S. PATENT DOCUMENTS

| | | | |
|---|---|---|---|
| 4,112,933 A | 9/1978 | Moses | |
| 4,314,551 A | 2/1982 | Kadell | |
| 4,360,008 A | 11/1982 | Corazzelli, Jr. | |
| 4,573,451 A | 3/1986 | Bauman | |
| 4,583,527 A | 4/1986 | Musicant et al. | |
| 4,611,579 A | 9/1986 | Bellhouse | |
| 4,705,024 A | 11/1987 | Bainton | |
| 4,827,910 A | 5/1989 | Mathews, III | |
| 4,924,855 A | 5/1990 | Salerno et al. | |
| 4,947,896 A | 8/1990 | Bartlett | |
| D312,308 S | 11/1990 | Abadir | |
| D312,500 S | 11/1990 | Abadir | |
| 5,003,962 A | 4/1991 | Chol | |
| 5,036,835 A | 8/1991 | Filli | |
| 5,063,907 A | 11/1991 | Musicant et al. | |
| 5,406,941 A * | 4/1995 | Roberts | 600/194 |
| 5,498,231 A | 3/1996 | Franicevic | |
| 5,536,245 A | 7/1996 | Dahlbeck | |
| 5,575,758 A | 11/1996 | Easterbrook, III | |
| 5,584,795 A | 12/1996 | Valenti | |
| 5,776,053 A | 7/1998 | Dragisic et al. | |
| 5,938,591 A | 8/1999 | Minson | |
| D413,977 S | 9/1999 | Cranton et al. | |
| 5,984,863 A | 11/1999 | Ansari | |
| 5,993,383 A * | 11/1999 | Haase | 600/191 |
| 6,095,972 A * | 8/2000 | Sakamoto | 600/190 |
| 6,139,491 A | 10/2000 | Heine et al. | |
| 6,217,514 B1 | 4/2001 | Gruen et al. | |
| 6,231,505 B1 | 5/2001 | Martin | |
| RE37,861 E | 9/2002 | Schneider | |
| 6,494,828 B1 | 12/2002 | Berall | |
| 6,623,425 B2 | 9/2003 | Cartledge et al. | |
| 6,666,819 B2 | 12/2003 | Heine et al. | |
| 2004/0034281 A1 | 2/2004 | Cartledge et al. | |
| 2004/0215062 A1 | 10/2004 | Dalle et al. | |

* cited by examiner

*Primary Examiner*—Matthew J Kasztejna (57) ABSTRACT

An improved laryngoscope. In one embodiment a laryngoscope blade includes a main blade portion and blade tip and a blade base. The main blade portion has a posterior surface, a distal end and proximal end. The blade tip extends from the distal end of the main blade portion. The blade tip also has a width that is flared wider in a first direction than a width of the main blade portion. The blade tip is further positioned at a select angle with relation to the posterior surface of the main blade portion. The blade base coupled to the proximal end of the blade.

5 Claims, 6 Drawing Sheets

LARYNGOSCOPE BLADE

TECHNICAL FIELD

The present invention relates generally to medical devices and in particular laryngoscopes.

BACKGROUND

A laryngoscope is a medical device that is used to position an endotrachel tube into a patient's trachea. In particular, a laryngoscope is used to expose a patient's aditus of the larynx thereby allowing the insertion of an endotracheal tube past the patient's vocal cords into the patient's trachea. The insertion of an endotracheal tube provides an airway for ventilation and prevents foreign substances from entering the patient's trachea and lungs.

Generally, traditional laryngoscopes with straight and curved blades do an adequate job in exposing the aditus of the larynx. In particular, a straight laryngoscope blade is typically used to lift a patient's epiglottis to expose the aditus of the larynx. However, the straight blade takes up relatively a lot of space in the patient's mouth and throat and can hamper a visual pathway to the epiglottis. The curved blade is typically used to displace the entire glottis structure anteriorly to expose the aditus of the larynx. An example of a curved blade is the MacIntosh blade (U.S. Pat. No. 2,354,474). However, in some cases these traditional laryngoscopes do not work efficiently because of injury or the patient's anatomy. An improved laryngoscope blade having a flared distal end and a cutout sidewall section near the proximal end of the blade was disclosed by the present inventor in U.S. Pat. No. 6,095,972 which is herein incorporated by reference. There is a desire in the art to have a further improved laryngoscope blade that is efficient in routine as well as non-routine intubations.

For the reasons stated above and for other reasons stated below which will become apparent to those skilled in the art upon reading and understanding the present specification, there is a need in the art for an improved laryngoscope blade that is efficient in routine as well as non-routine intubations.

SUMMARY

The above-mentioned problems and other problems are resolved by the present invention and will be understood by reading and studying the following specification.

In one embodiment, a laryngoscope blade is disclosed. The laryngoscope blade includes a main blade portion and blade tip and a blade base. The main blade portion has an posterior surface, a distal end and proximal end. The blade tip is coupled to the distal end of the main blade portion. The blade tip also has a width that is flared wider in a first direction than a width of the main blade portion. The blade tip is further positioned at a select angle with relation to the posterior surface of the main blade portion. The blade base coupled to the proximal end of the blade.

In another embodiment, another laryngoscope blade is disclosed. The laryngoscope blade includes a main blade portion, a first tongue displacement plate, a second tongue displacement plate and a blade base. The main blade portion has a distal end and a proximal end. The first tongue displacement plate has a first end extending from a first side of the main blade portion. Moreover, the first tongue displacement plate further extends along a select length of the main blade portion that is proximate the distal end of the main blade portion. The second tongue displacement plate extends from a second end of the first tongue displacement plate in a direction away from the main displacement blade. The first tongue displacement plate and the second tongue displacement plate being adapted to work together to displace a patient's tongue. The blade base is coupled to the proximal end of the main blade portion. The blade base is adapted to selectively couple a laryngoscope handle to the laryngoscope blade.

In further another embodiment, another laryngoscope blade is disclosed. The blade includes a main blade portion, a blade tip, first and second tongue displacement plates and a blade base. The main blade portion has a posterior surface, a distal end and a proximal end. The blade tip extends from the distal end of the main blade portion. The blade tip further extends beyond a width of the main blade portion from a first side of the main blade portion. The blade tip yet further extends from the posterior surface of the main blade portion at a select angle. The first tongue displacement plate extends from a second side of the main blade portion at generally a right angle. The first tongue displacement portion further extends along a select length of the main blade portion proximate the distal end of the main blade portion. A second tongue displacement plate extends from the first displacement plate at generally a right angle. The second displacement plate further extends from the first displacement plate in a direction that is generally away from the main blade portion. The blade base is coupled to the proximal end of the main blade portion.

In yet another embodiment a laryngoscope is disclosed. The laryngoscope includes a laryngoscope handle and a laryngoscope blade. The laryngoscope blade includes a main blade portion, a blade tip, first and second tongue displacement plates and a blade base. The main blade portion has an posterior surface, a distal end and a proximal end. The blade tip extends from the distal end of the main blade portion. The blade tip further extends beyond a width of the main blade portion from a first side of the main blade portion. The blade tip yet further extends from the posterior surface of the main blade portion at a select angle. The first tongue displacement plate extends from a second side of the main blade portion at generally a right angle. The first tongue displacement portion further extends along a select length of the main blade portion proximate the distal end of the main blade portion. A second tongue displacement plate extends from the first displacement plate at generally a right angle. The second displacement plate further extends from the first displacement plate in a direction that is generally away from the main blade portion. The blade base is coupled to the proximal end of the main blade portion. Moreover, the blade base is adapted to be selectively coupled to the laryngoscope handle.

In still yet another embodiment, a method of using a laryngoscope is disclosed. The method comprises inserting a laryngoscope blade into a patient's oral cavity. Displacing a patient's tongue with first and second displacement plates located proximate a distal end of the laryngoscope blade. Positioning a proximal end of the laryngoscope blade proximate a patients upper teeth and exposing the patient's aditus of larynx.

BRIEF DESCRIPTION OF THE DRAWINGS

The present invention can be more easily understood and further advantages and uses thereof more readily apparent, when considered in view of the description of the preferred embodiments and the following figures in which.

In accordance with common practice, the various described features are not drawn to scale but are drawn to emphasize specific features relevant to the present invention. Reference characters denote like elements throughout Figures and text.

DETAILED DESCRIPTION

In the following detailed description of the preferred embodiments, reference is made to the accompanying drawings, which form a part hereof, and in which is shown by way of illustration specific preferred embodiments in which the inventions may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense, and the scope of the present invention is defined only by the claims and equivalents thereof.

Embodiments of the present invention provide a laryngoscope blade that is more efficient and effective than standard blades. The embodiments also provide a single laryngoscope that can replace both standard straight blades and standard curved blades. In particular, the angled tip in combination with the relatively shallow blade at a proximal end of the blade allows embodiments of the present invention to be used in a manner that practitioners are accustom to with regard standard curved blades as well as with standard straight blade thereby creating a single blade that can be used in almost all situations.

Figure 1:
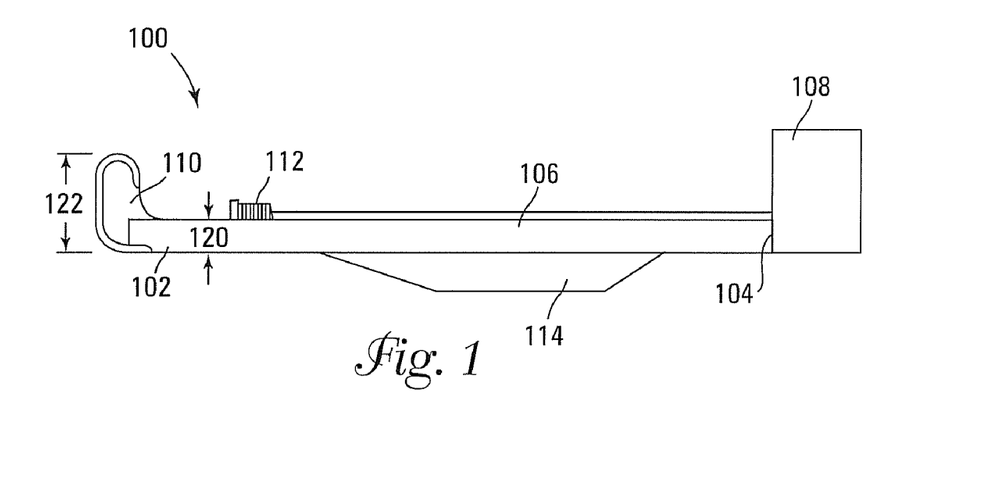
FIG. 1 is a top view of one embodiment of a laryngoscope blade of the present invention.

FIG. 1 illustrates a top view of one embodiment of a laryngoscope blade 100 of the present is illustrated. As illustrated, this embodiment includes a main blade portion 106, a blade base 108 and a blade tip 110. Also illustrated is a light source 112 coupled to the main blade portion 106. The blade tip 110 extends from the distal end 102 of the main blade portion 106. As illustrated, the blade tip 110 is flared out beyond a width 120 of the main blade portion 106. The blade tip 110 having a width 122 that extends beyond the width 120 of the blade 106 allows for a slimmer blade than is typically used in the prior art which adds in the maneuverability of the blade 100 during use. Moreover, the relatively thin main blade portion 106 allows for better visability than a standard blade and also provides for greater space for larger endotracheal tubes such as double lumenum endotracheal tubes for single lung ventilation. The blade base 108 extends from a proximal end 104 of the main blade portion 106. In this embodiment, a second tongue displacement plate 114 extends out from an opposite side of the main blade portion 106 as the blade tip 110. The second tongue displacement plate 114 is adapted to displace a patients tongue during use.

Figure 2:
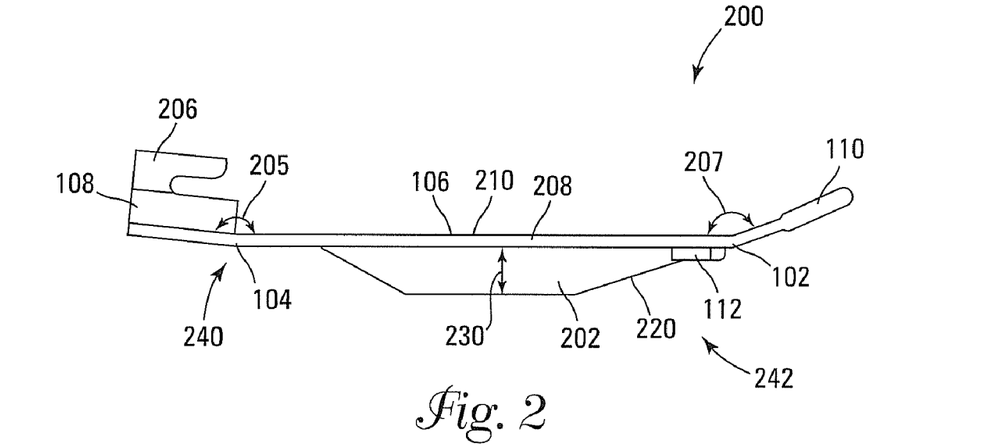
FIG. 2 is a side view of another embodiment of a laryngoscope blade of the present invention.

Referring to FIG. 2, a side view of another embodiment of a laryngoscope blade 200 of the present invention is illustrated. The blade 200 has a proximal end 104, a main blade portion 106 which has a mid portion 208 and a distal end 102. FIG. 2 illustrates that the blade base 108 includes a handle connector portion 206 which is adapted to selectively couple to a standard laryngoscope handle. Also illustrated is a first tongue displacement plate 202 that extends down from the main blade portion 106. The first tongue displacement plate 202 extends along a length of the main blade portion 106. However, as illustrated, the first tongue displacement plate 202 does not extend all the way back to proximal end 104 of the main blade portion 106. That is, the first tongue displacement plate has a first cutout portion 240 approximate the proximal end. In particular, the first cutout portion 240 allows for added clearance in relation to a patient's top teeth during use of the laryngoscope 200. The first tongue displacement plate 202 further has a tapered distal portion 220 that tapers down from a maximum width 230 of the first tongue displacement plate 202 to proximate the distal end of 102 of the main blade portion 106. That is, the side displacement portion has a second cutout portion 242 adjacent the distal end 204 of the blade 106. This tapered portion (cutout portion 242) also allows for the added maneuverability of the laryngoscope 200.

Also illustrated in this embodiment of the laryngoscope 200 of FIG. 2 is that the proximal end 104 and distal end 102 of the blade 106 are position at select angles with respect to an posterior surface 210 of the main blade portion 106. In particular, the proximal end 104 of the blade 106 is at angle 205 with respect the posterior surface 210 of the blade 106 and the distal end 102 of the blade 106 is at angle 207 with respect the posterior surface 210 of blade 106. Angles 205 and 207 are obtuse angles. Angles 205 and 207 allow for added leverage in exposing the aditus of the larynx of a patient during use of the laryngoscope 200.

Figure 3:
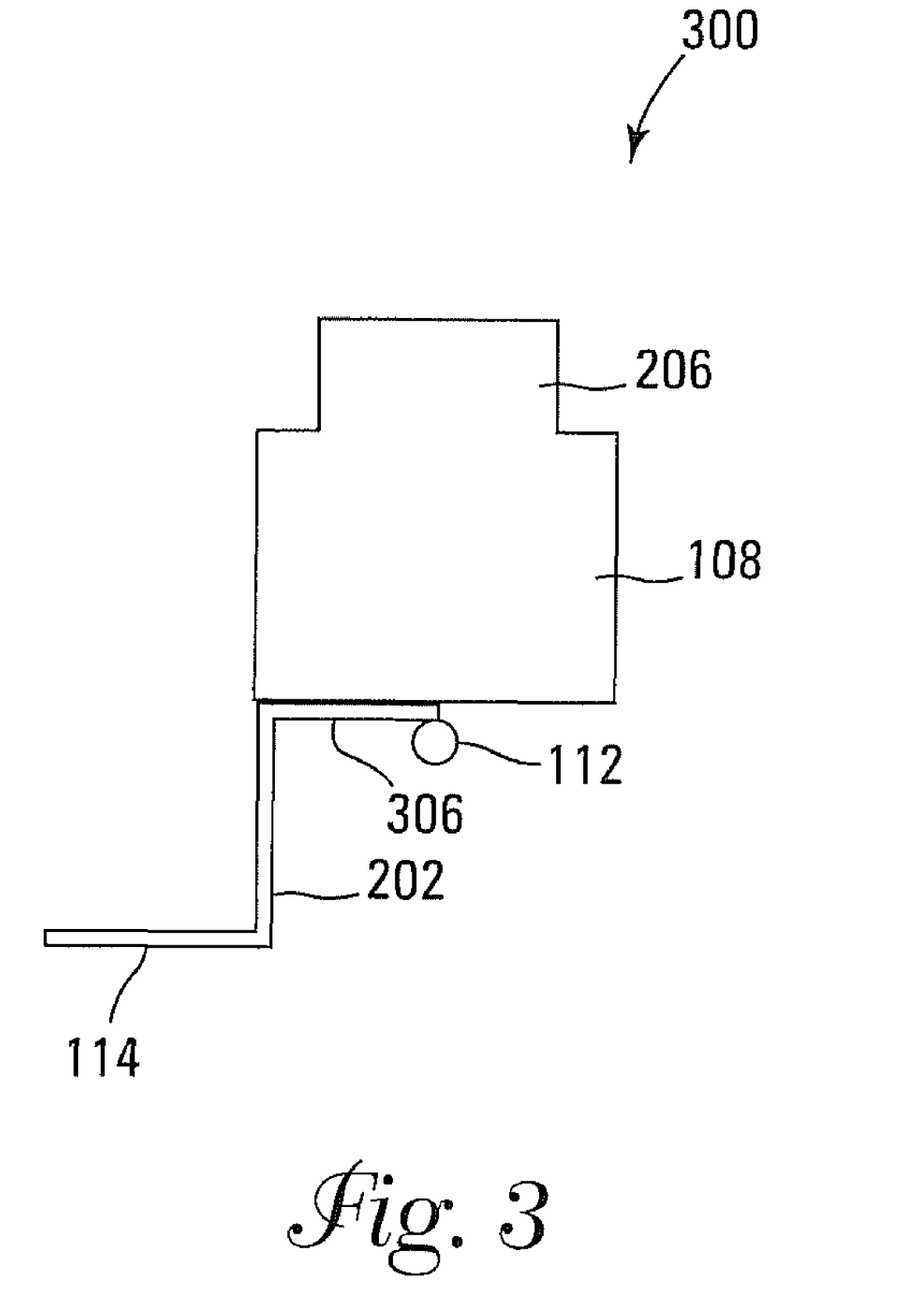
FIG. 3 is a back view of a laryngoscope blade of one embodiment of the present invention.

FIG. 3 illustrates a back view of a laryngoscope blade 300 of one embodiment of the present invention. As illustrated, the blade base 108 includes a handle connection portion 206. In this embodiment, a connection plate 306 couples a main blade portion 106 to the blade base 108. Also illustrated in FIG. 3 are the first tongue displacement plate 202 and the second tongue displacement plate 114. As illustrated, in this embodiment, the second tongue displacement plate 114 is coupled to extend away from the first tongue displacement plate 202 in a direction that is away from the main blade portion 106. Moreover, the second tongue displacement plate 114 is coupled to a side of the first tongue displacement plate 202 that is opposite the side the first tongue displacement plate 202 is coupled to the main blade portion 106. In addition, as illustrated in this embodiment, the second tongue displacement plate 114 extends away from the first tongue displacement plate at generally a perpendicular angle. The first tongue displacement plate 202 and the second tongue displacement plate 114 are adapted to work together the move the tongue of the patent out of the way during use of the laryngoscope 300.

Figure 4:
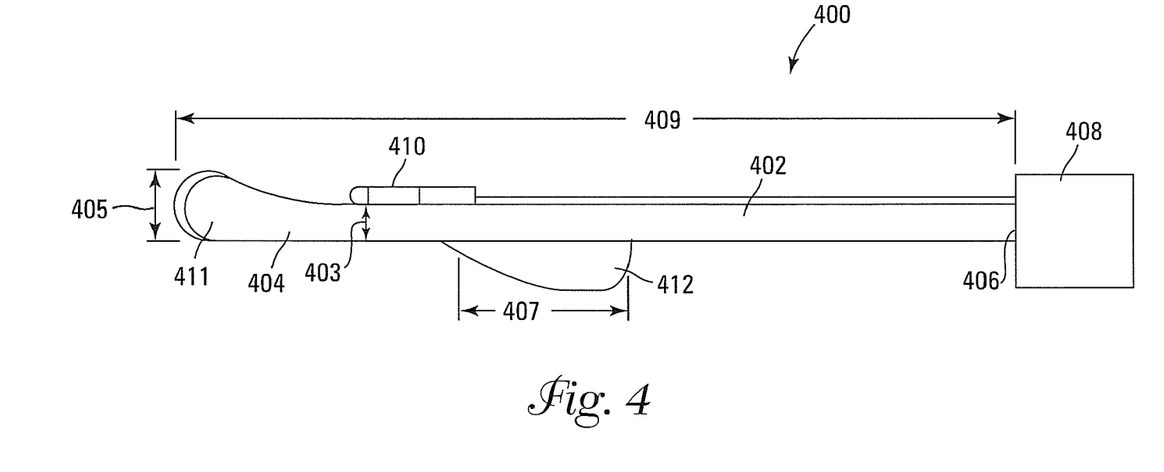
FIG. 4 is a top view of yet another laryngoscope blade of the present invention.

Another embodiment of a laryngoscope blade 400 is illustrated in the top view of FIG. 4. As illustrated, this embodiment includes a main blade portion 402, a blade tip 411 that is located at a distal end 404 of the main blade portion 402, a blade base 408 that is coupled to a proximal end 406 of the main blade portion 402 and a light source 410. The blade tip 411 has a tip width 405 that is wider than the main blade portion width 403. Also illustrated in FIG. 4 is a second tongue displacement plate 412 that is adapted to displace the tongue of a patient when using the laryngoscope 400. In this embodiment, the second tongue displacement plate 412 has a displacement length 407 that is significantly less than the main blade portion length 409. In one embodiment, the displacement length 407 is less than half the length of the main blade portion length 409. This allows for better maneuverability of the laryngoscope blade 400 and provides a better viewing channel.

Figure 5:
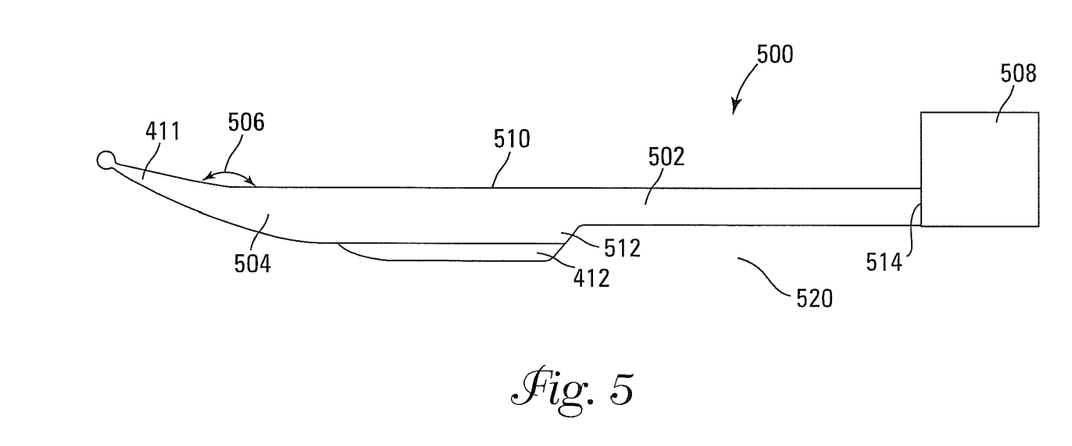
FIG. 5 is a side view of a laryngoscope blade of one embodiment of the present invention.

A side view of another embodiment of a laryngoscope blade 500 is illustrated in FIG. 5. As illustrated, this laryngoscope blade 500 includes a main blade portion 502, a blade base 508 coupled to the main blade portion 502 at a proximal end 514 of the main blade portion 502 and a blade tip 411 extending from a distal end 504 of the main blade portion 502. The main blade portion 502 has an posterior surface 510 that extends along the length of the main blade portion 502. As illustrated in this embodiment, the blade tip 411 extends from the distal end 504 of the main blade portion 502 at a select obtuse angle 506 from the posterior surface 510 of the main blade portion 502. In one embodiment, angle 506 is about 165 degrees. However, it will be understood in the art that angle 506 can vary depending on the length of the main blade portion 502 and the depth of cutout portion 520. Cutout portion 520 is described in further detail below.

Also illustrated in FIG. 5 is first tongue displacement plate 512 and the second tongue displacement plate 412. In one embodiment, the first tongue displacement plate 512 extends from the blade 502 from a side of the blade 502 that is opposite of a side in which the blade tip 411 flares out wider than width of the main blade portion 502. As with the other embodiments of the present invention, the first tongue displacement plate 512 and the second tongue displacement plate 412 work together to displace the tongue of a patent. Both the first and second tongue displacement plates 512 and 412 are located proximate the distal end 504 of the main blade portion 502. In one embodiment, the length of the first tongue displacement plate 512 and the second tongue displacement plate 412 is less than half of the length of the blade 502. By having the length of the first tongue displacement plate 512 and the second tongue displacement plate 412 less than the length of the blade 502, a cutout portion 520 is created that provides clearance for a patient's teeth during use. Moreover, the relatively short length of the first tongue displacement plate 512 and the second tongue displacement plate 512 allow for added maneuverability and a better channel of view. The angled blade tip 411 and the cutout portion 520 of the laryngoscope work together to provide added maneuverability. In fact, one of the advantages of these features is that laryngoscope 500 can be used as a traditional curved blade (i.e. the cutout portion and the tip angel 506 replicate the functions of the traditional curved blade). Laryngoscope 500 can also be used as a traditional straight blade. Accordingly, a single embodiment of the present invention can replace both the traditional as well as the curved blades.

Figure 6:
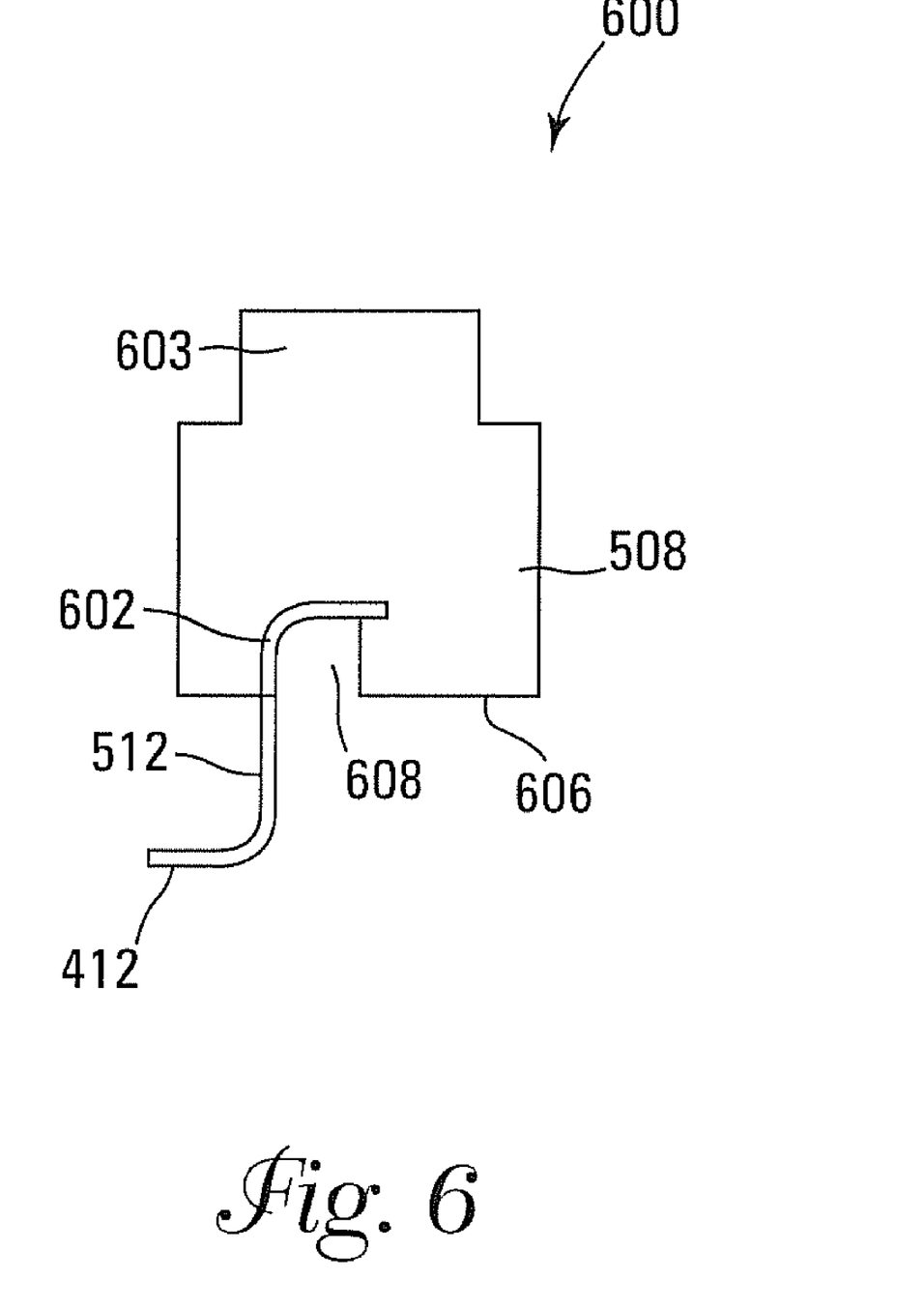
FIG. 6 is a back view of a laryngoscope blade of one embodiment of the present invention.

Referring to FIG. 6, a back view of one embodiment of a laryngoscope 600 of the present invention is illustrated. This back side illustration of the laryngoscope 600 is similar to the laryngoscopes of FIGS. 5 and 4. FIG. 6 illustrates a handle connection portion 603 of the blade base 508. Also illustrated is the blade connector plate 602 that is coupled to blade base 508. Also illustrated are the first tongue displacement plate 512 and the second tongue displacement plate 412. As illustrated, the blade connector plate 602 and a main blade portion 504 in this embodiment is curved. Also illustrated in FIG. 6 is the second tongue displacement plate 412 extending from the first tongue displacement plate 512 at approximately a perpendicular angle. One aspect of this embodiment, as shown, is that the blade connection portion 602 is connected to the blade base 508 in such a manner that is does not extend beyond the depth of the blade base 508. This allows for added top teeth clearance in the cutout section 520. In particular, in this embodiment, a bottom portion 606 of the blade base 502 has a channel 608 upon which the blade connection plate 602 of the main blade portion 502 is received.

Figure 7:
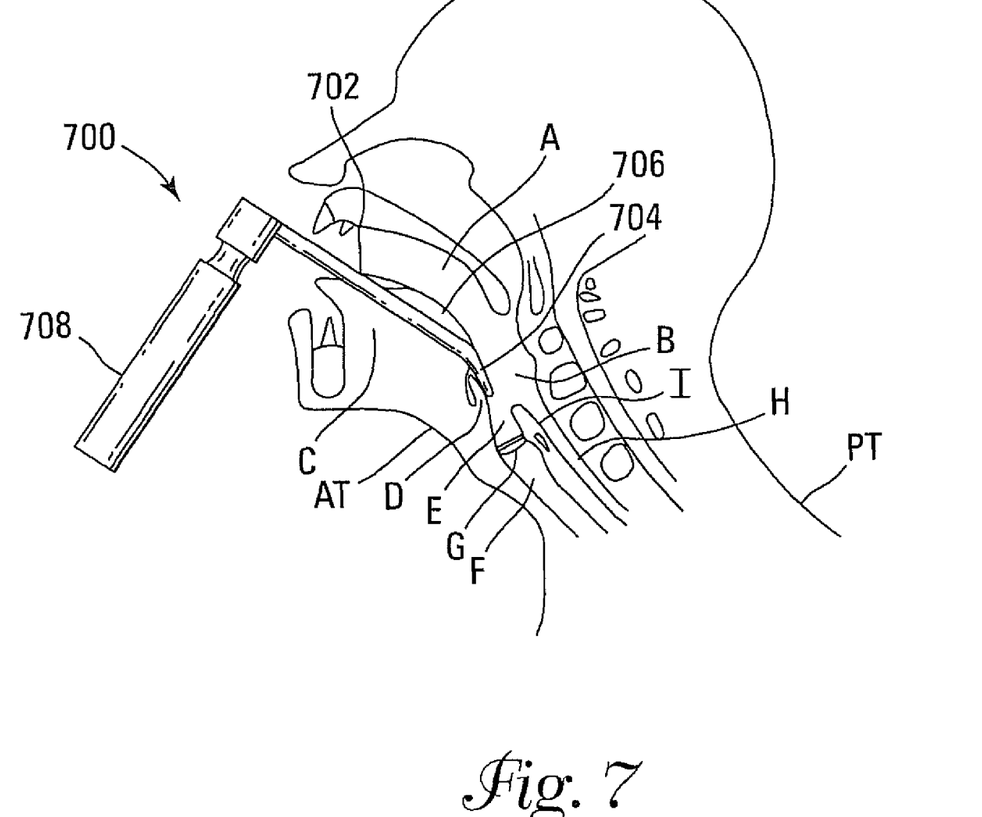
FIG. 7 is a side view of one embodiment of the present invention in use.

Referring to FIG. 7, a method of using a laryngoscope 700 having a laryngoscope blade 702 of one embodiment of the present invention is illustrated. In particular, a patient is illustrated as having an oral cavity (A), a laryngopharynx (B), a tongue (C), an epiglottis (D), an aditus of larynx (E), a trachea (F), vocal cords (G), an esophagus (H) and a cricoid cartilage ring (I). Also illustrated is the anterior direction (AT) and the posterior direction (PT). In this method, the user grasps the handle 708 and inserts the laryngoscope blade 702 into the oral cavity (A) of the patient. The tongue displacement plate 706, which is located proximate a distal end of the laryngoscope blade 702, engages the tongue C to move the tongue C out of a viewing channel. The flared blade tip 407 is then positioned under the epiglottis (D). The epiglottis (D) is then lifted away to expose the aditus of larynx (E) by rotating the blade 702 into the epiglottis (D). Lifting the epiglotottis (D) away from the aditus of larynx (E) is how a typical straight blade it used. However, the relatively shallow blade 702 at a proximal end provides added top teeth clearance during rotation with the preset invention. Moreover, the relatively thin blade 702 with a flared blade tip 704 provides added maneuverability and visibility.

Figure 8:
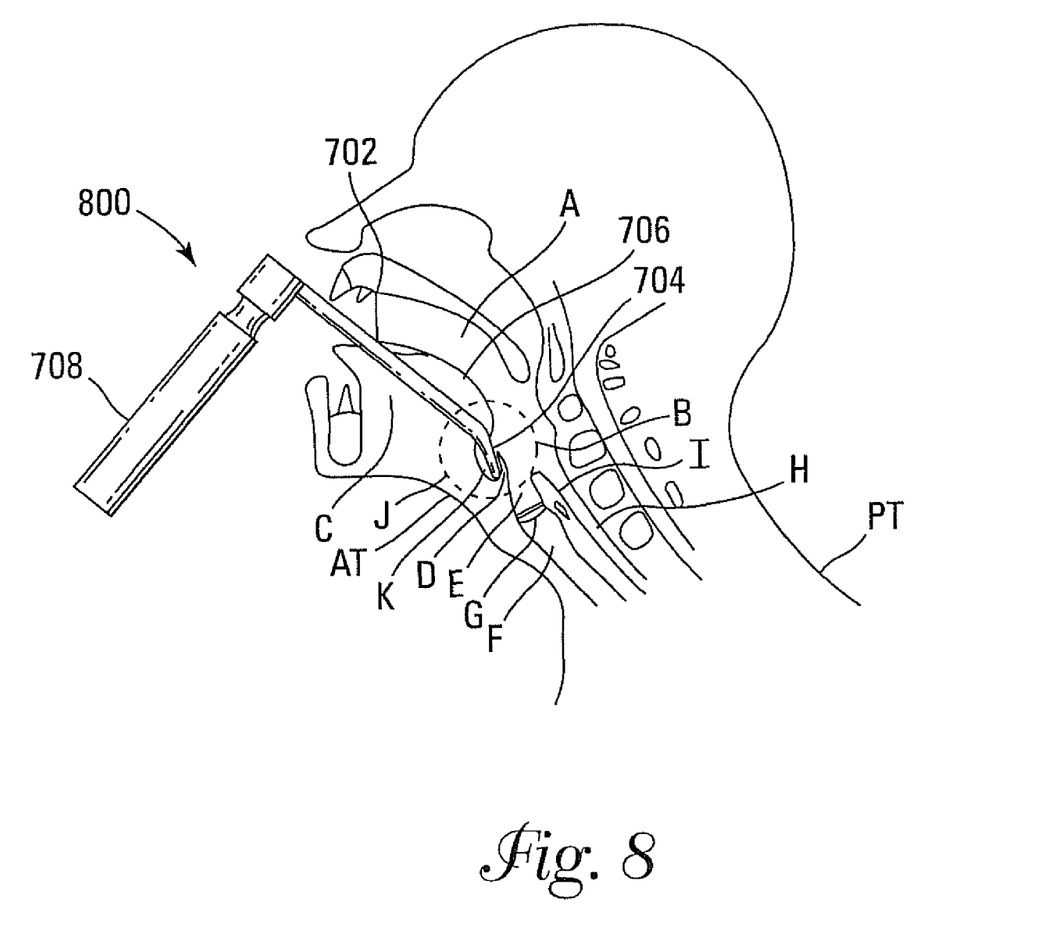
FIG. 8 is also a side view of one embodiment of the present invention in use.

Another method of using a laryngoscope 800 having a laryngoscope blade 702 of the present invention is illustrated in FIG. 8. In this embodiment, once the laryngoscope blade 702 is inserted in the oral cavity, the blade tip is inserted into the vallecula (K) of the patient. The tongue displacement plate 706, which is located proximate a distal end of the laryngoscope blade 702, engages the tongue (C) to move the tongue (C) out of a viewing channel. The laryngoscope 800 is then lifted upward and forward without changing the angle of the blade. This action lifts the entire glottis structure (J) which in turn exposes the aditus of larynx (E). The relatively shallow blade 702 at a proximal end provides added top teeth clearance. This added top teeth clearance along with angle of the blade tip 407 allows embodiments of the present invention to exposes the aditus of larynx (E) as a typical curved blade would. However, the relatively thin blade 702 with a flared blade tip 704 provides added maneuverability and visability not found in a typical curved blade.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:

1. A laryngoscope blade, the blade comprising:
   a main blade portion having a posterior surface, a distal end and a proximal end, the posterior surface having a length that is generally straight from the proximal end to the distal end;
   a blade tip extending from the distal end of the main blade portion, the blade tip further extending beyond a width of the main blade portion from a first side of the main blade portion, the blade tip further extending from the posterior surface of the main blade portion at a select angle;
   a first tongue displacement plate extending from a second side of the main blade portion at generally a right angle, the first tongue displacement portion further extending along a select length of the main blade portion proximate the distal end of the main blade portion;

a second tongue displacement plate extending from the first displacement plate at generally a right angle, the second displacement plate further extending from the first displacement plate in a direction that is generally away from the main blade portion, the second tongue displacement plate further having a surface that is positioned in an opposite direction as the posterior surface of the main blade, the surface of the second tongue displacement plate forming a plane that is generally parallel with an axis formed by the length of the posterior surface; and a blade base coupled to the proximal end of the main blade portion, wherein the generally straight length of the posterior surface extends from the blade base at generally a right angle.

2. The blade of claim 1, wherein the first tongue displacement plate has a length that is less than ½ the length of the main blade portion.

3. The blade of claim 1, wherein the select angle between the blade tip and the posterior surface is an obtuse angle.

4. The blade of claim 1, wherein the select angle between the blade tip and the posterior surface is approximately 165 degrees.

5. The blade of claim 1, further comprising:

the blade base has a channel; and a blade connection portion coupled to the proximal end of the main blade portion, the blade connection portion received in the channel in the blade base.

* * * * *